US00PP27776P3

(12) United States Plant Patent
Byrne et al.

(10) Patent No.: US PP27,776 P3
(45) Date of Patent: Mar. 14, 2017

(54) PEACH TREE NAMED 'FLAT DELIGHT TWO'

(50) Latin Name: *Prunus persica*
Varietal Denomination: Flat Delight Two

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 122 days.

(21) Appl. No.: 14/544,502

(22) Filed: Jan. 13, 2015

(65) Prior Publication Data

US 2016/0205842 P1 Jul. 14, 2016

(51) Int. Cl.
*A01H 5/08* (2006.01)

(52) U.S. Cl.
USPC ..... Plt./197

(58) Field of Classification Search
USPC ..... Plt./197, 198
See application file for complete search history.

(56) References Cited

PUBLICATIONS

The Brooks and Olmo Register of Fruit and Nut Varieties, 3rd Ed., American Society of Horticultural Science Press, Alexandria, VA, 1997.

*Primary Examiner* — Anne Grunberg
(74) *Attorney, Agent, or Firm* — Ramey & Schwaller, LLP

(57) ABSTRACT

Disclosed is a new variety of *Prunus persica* named 'Flat Delight Two'. This new variety, which requires 500-550 chilling units of dormancy, is considered to be a peach tree of early mid-season maturity, which produces yellow-fleshed, sub-acid flat (donut, pantao) fruit that are firm, attractively colored, and suitable for local fresh market and home garden use.

5 Drawing Sheets

BACKGROUND OF THE INVENTION

Field of the Invention

This invention relates to peach trees referred to as a variety of *Prunus persica* named 'Flat Delight Two'. 'Flat Delight Two', is a sub-acid, yellow-fleshed flat peach which requires 450-500 chilling units of dormancy, produces high quality, firm semifreestone peach that matures in early June in the medium chill zone of Texas.

SUMMARY OF THE INVENTION

The 'Flat Delight Two' peach which is adapted to the medium chill zone where cultivars such as 'TexKing' (Byrne and Bacon, 2004, U.S. Plant Pat. No. 14,627. Mar. 23, 2004), 'TexRoyal' (Byrne and Bacon, 1991, unpatented), and 'June Gold' (Brooks, 1958, unpatented) are adapted. The new peach produces sub-acid, yellow-fleshed, flat-shaped (pantao or donut) fruit that ripens in the early June in the medium chill zone of Texas. It has fruit that is of high quality, firm and with an attractive coloration.

ORIGIN OF THE VARIETY

The present peach tree was the result of an ongoing Stone Fruit Breeding Program of Texas A & M University, College Station, Brazos County, Tex. To this end, both controlled crosses are made each year to produce seedling populations from which improved progenies are evaluated and selected.

The seedling TX3D353LP ('Flat Delight Two') was discovered at the Texas A & M University Horticultural Farm in College Station, Tex. in 2007, and was chosen from a population of seedlings that resulted from seed from a cross between unpatented peach 'Flordacrest' (Sherman and Lyrene, 1989) and the patented white fleshed, subacid pantao peach 'Stark Saturn' (Mehlenbacher et al., 1985; U.S. Plant Pat. No. 5,123) which was released by the Fruit Breeding Program at Rutgers University. Resulting seed from this cross were planted in 2004 at the Texas A & M University Horticultural Farm in College Station, Tex. The seedling designated as TX3D353LP was propagated for subsequent observation. Two-year and older trees of the variety were subsequently evaluated during the 2009 through 2013 fruit growing seasons in Texas (Floresville, College Station, Fairfield).

The new variety 'Flat Delight Two' differs from its yellow fleshed, low chill, round shaped peach female parent 'Flordacrest' in that it requires more chilling hours to break dormancy, blooms 3-5 days later, ripens 7-10 days later and has a fruit that has a flat shape.

The new variety 'Flat Delight Two' differs from 'Stark Saturn' its white fleshed pantao (flat shape) peach pollen parent in that it has yellow flesh, requires less chilling accumulation to break dormancy, blooms 12-16 days earlier and ripens 12-16 days earlier.

This is the first medium chill medium chill, subacid, yellow fleshed pantao released for the medium chill region of the southeastern USA. It differs from the unpatented white-fleshed, subacid, pantao cultivar, 'Galaxy' that was released by the USDA in Fresno, Calif. (Ramming, 2005, not patented) as it has yellow flesh. It is similar to 'Galaxy' with respect to its shape, subacid flavor, chilling requirement, and ripening season.

ASEXUAL REPRODUCTION OF THE VARIETY

'Flat Delight Two' was bud grafted onto virus-free Nemaguard ("The Brooks and Olmo Register of Fruit and Nut Varieties," 3rd Ed., American Society of Horticultural Science Press, Alexandria, Va., 1997, unpatented) peach rootstock in June 2007 at the nursery site in Oakdale, Calif. The variety was subsequently planted at the experimental orchard in three sites in Texas (Fairfield, College Station and Floresville). Fruit from the resulting propagation has been evaluated during the period from 2009-2013 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
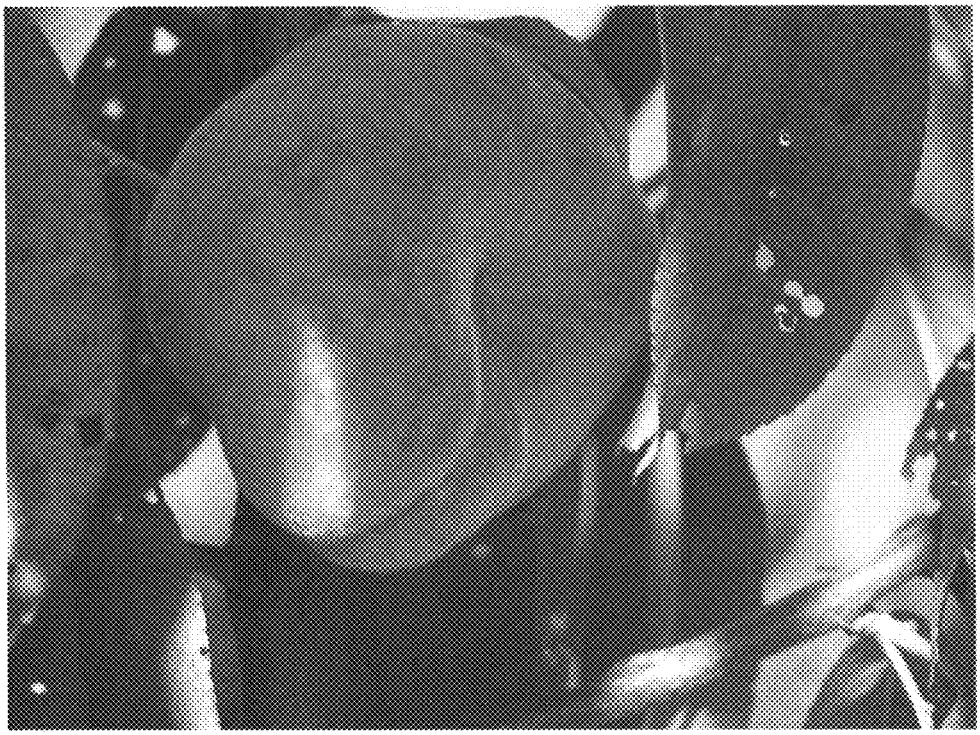
FIG. 1. Fruit of 'Flat Delight Two' showing the red blush over the yellow ground color and flat fruit shape. The fruit is on a tree in the experimental orchard in Fairfield, Tex.
Figure 2:
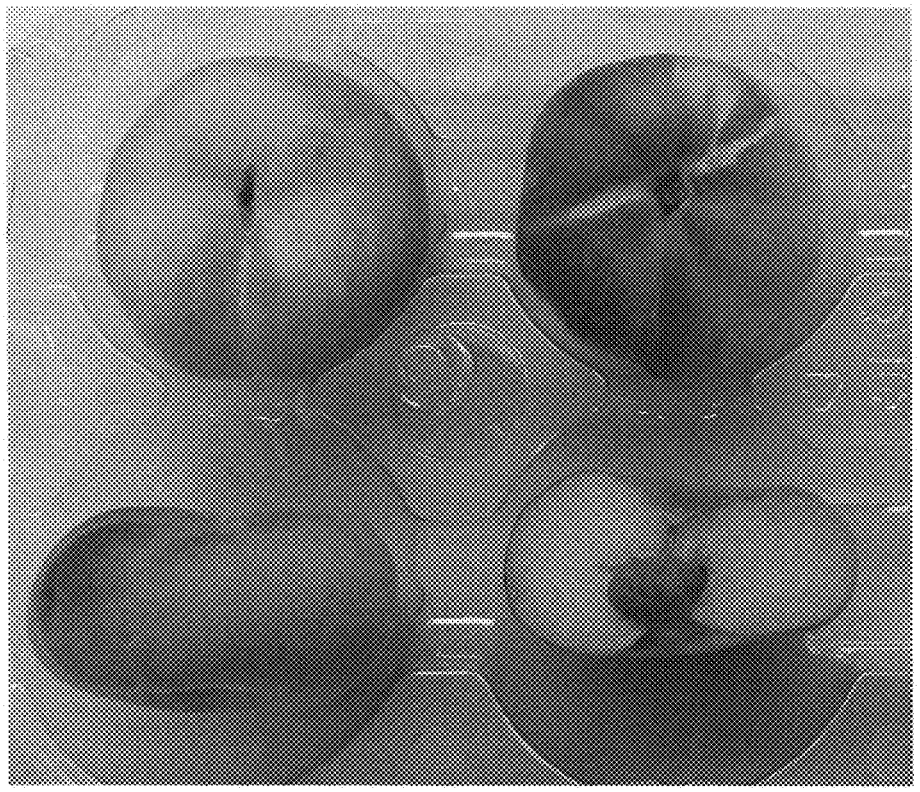
FIG. 2. Color photograph of 'Flat Delight Two' fruit showing the pit and its semifreestone attachment, internal flesh color, shape, and external coloring. The fruit was harvested in the research plots in Fairfield, Tex.
Figure 3:
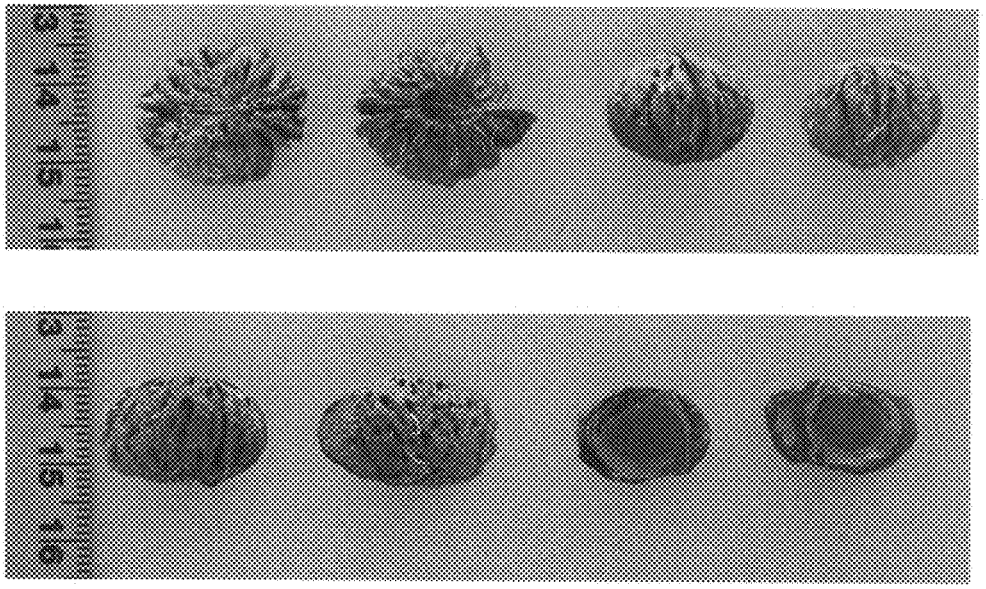
FIG. 3. Photographs of the endocarp of 'Flat Delight Two' to show the flat shape. The pits in the picture are discolored and not their original color. The ruler is demarcated in millimeters.
Figure 4:
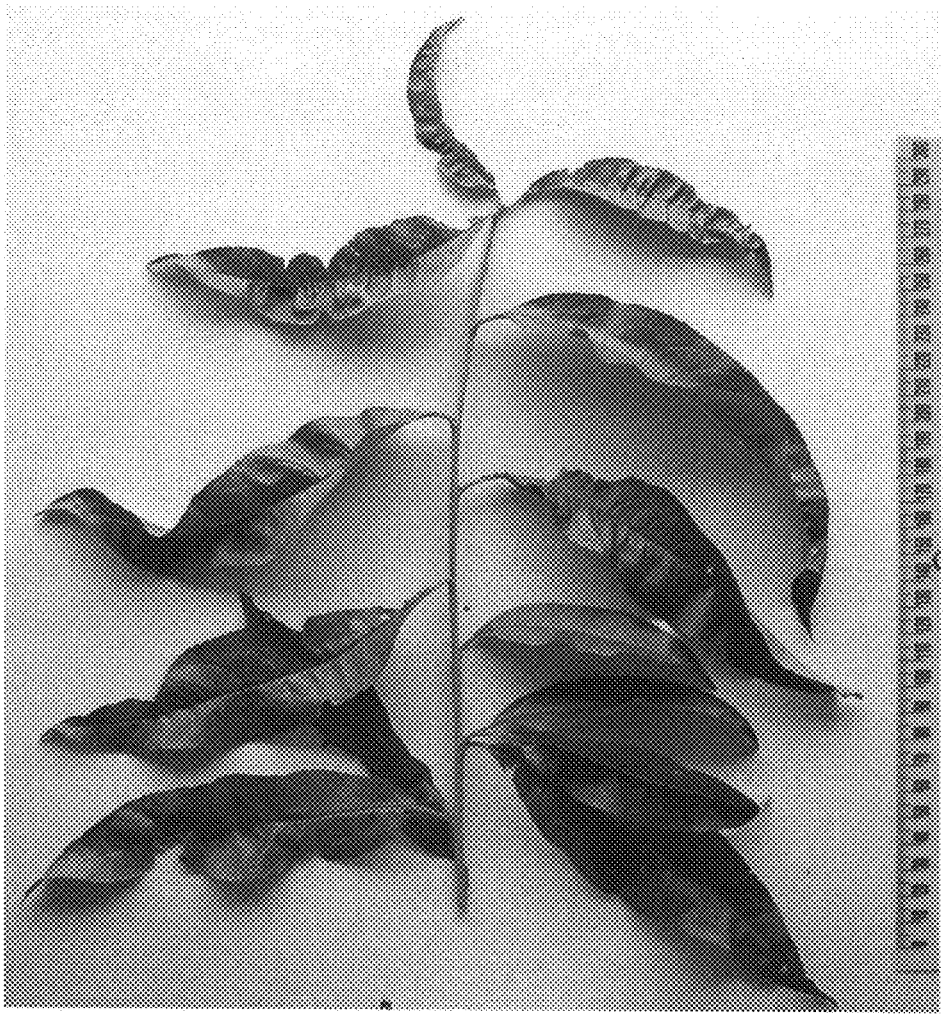
FIG. 4. A stem showing the leaves of the 'Flat Delight Two' peach. The ruler is demarcated in millimeters.
Figure 5:
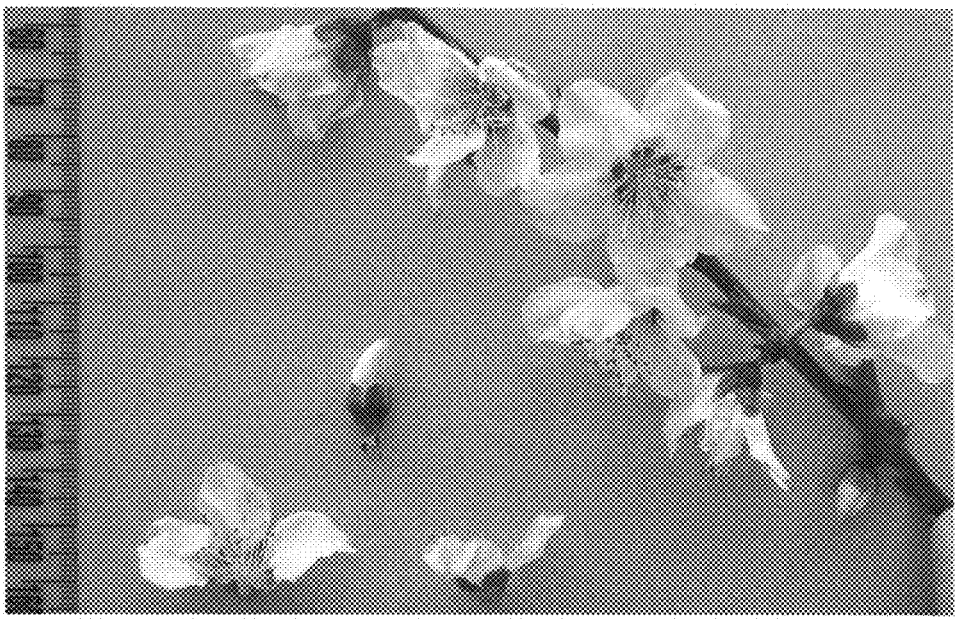
FIG. 5. Showy flowers of 'Flat Delight Two'. The ruler is in millimeters.

Referring to the pomological details of this new and distinct variety of peach tree, the following has been observed under the ecological conditions prevailing at the experimental orchards in the medium chill zone of Texas. All major color code designations are by reference to The R.H.S. Colour Chart (Third Edition) provided by The Royal Horticultural Society of Great Britain. Colors are approximate as color depends on horticultural practices such as light level and fertilization rate, among others.

Tree:

*Size*.—Generally average to above average as compared to other common peach cultivars.

*Height*.—10 feet (3.05 m) at the end of the 2013 growing season.

*Width*.—11 feet width (3.35 m) at the end of the 2013 growing season.

*Vigor*.—High.

*Density*.—Medium to high.

*Productivity*.—Productive.

*Shape*.—The trees are vigorous with the typical semi-spreading growth habit similar to 'TexKing', 'TexPrince' (Byrne and Bacon, 2004; U.S. Plant Pat. No. 14,629. Mar. 23, 2004), and 'TexRoyal'.

*Current season growth*.—The current season growth for the new variety was approximately 3.6 to 4.3 feet (1.1-1.3 m).

*Regularity of bearing*.—Good and considered hardy under the climatic conditions of the medium chill zone of Texas and the central San Joaquin Valley, Calif.

Trunk:

*Size*.—Approximately 13.5 inches (34.3 cm) in diameter and 4 inches (10.2 cm) in circumference when measured at a distance of approximately 12 inches (30.5 cm) above the soil level, at the end of the 2013 growing season on an eight-year old tree.

*Bark texture*.—Considered moderately rough with numerous folds of papery scarf-like skin being present.

*Bark coloration*.—Variable, colors present are N155B of the White Group, 156A-D of the Greyed-White Group, N187D of the Greyed-Purple Group, 197B-D of the Greyed-Green Group and N200D of the Brown Group.

Branches:

*Size*.—Considered medium for the variety.

*Thickness*.—Average (about 8 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 4 to 9 mm in width and were approximately 1 to 2 mm in height.

*Current season shoots*.—Surface texture — Substantially glabrous.

*Internode length*.—Approximately 3 to 4 cm as measured in the middle of a current season stem.

*Color of mature branches*.—The predominant colors are 166A and 176A-B of the Greyed-Orange Group, 198C-D of the Greyed-Green Group, and 200C and N200C of the Brown Group.

*Current season shoots*.—Color — Medium to light green (137A-B and 138C-D of the Green Group) with some reddish-brown coloration appearing on exposed surface of the shoots (177C-D of the Greyed-Orange Group). The color of new shoot tips is considered a bright and shiny green (mainly 146C-D of the Yellow-Green Group).

*Type of bearing*.—Long shoots only.

*Spur length*.—Not applicable.

*Vegetative bud size*.—Generally 1-2 mm in length on the mid portion of a summer shoot.

*Vegetative bud shape of apex*.—Acute.

*Position of vegetative bud in relation to one year old shoot*.—Adpressed.

Leaves:

*Size*.—Considered moderately large for the species. Leaf measurements have been taken from vigorous upright current season growth approximately at mid-shoot.

*Leaf length*.—Approximately 166 to 183 mm.

*Leaf width*.—Approximately 41 to 44 mm.

*Leaf thickness*.—Less than 1 mm.

*Leaf form*.—Lanceolate.

*Leaf tip form*.—Acuminate.

*Leaf upper surface color*.—Green, approximately 137A-B of the Green Group.

*Leaf lower surface color*.—Green, approximately 137C and 147B of the Green Group.

*Leaf mid-vein color*.—Light green, approximately 145C of the Yellow-Green Group.

*Leaf margins*.—Form — Considered crenate/crenulate. Uniformity — Considered generally uniform.

*Leaf petioles*.—Size — Considered medium long. Length — Approximately 11 to 14 mm. Thickness — Approximately 1.5 to 2 mm. Color — Pale green, approximately 145C of the Yellow-Green Group.

*Leaf glands* (*nectaries*).—Size — Approximately 1-3 mm in height and 1 mm in width. Number — Generally 1-3 per leaf. Type — Reniform. Position: predominantly on base of the leaf blade. Color — Light brown (164B-C and 165C of the Greyed-Orange Group).

*Leaf stipules*.—Size — medium long for the variety. Length — Approximately 10 to 12 mm. Form — Lanceolate. Color — Green (approximately 135D of the Green Group) with reddish brown tips (174B-D of the Greyed-Orange Group) when young. The stipules are considered to be early deciduous.

*Ratio of wood* (*leaf*) *buds to flowering buds*.—1 to 2 flower buds per vegetative bud.

Flowers:

*Floral buds*.—General — The floral buds are considered to be medium in size, conic in form, and slightly appressed relative to the bearing shoot. Color — The bud scales are red-brown, (approximately 185A-B of the Greyed-Purple Group and 200B-C of the Brown Group). The buds are considered hardy under the climatic conditions found in the medium chill zone of Texas and the central San Joaquin Valley, Calif. Length — Approximately 4 to 5 mm. Blooming Type — Considered relatively early in relation to other peach cultivars grown in the medium chill zone of Texas. Date of full bloom was between February 20th and February 26th during the period between 2010 and 2013. The average bloom was February 22nd during this time period 10-14 days before 'June Gold' and with or a few days after the medium chill peach 'TexKing'.

*Flower fertility*.—Self fertile.

*Flower type*.—Showy.

*Flower size*.—Flower diameter at full bloom is approximately 32 to 43 mm.

*Bloom quantity*.—Considered abundant.

*Flower bud frequency*.—Normally 1 to 2 per node.

*Petal size*.—General — Considered medium large to large for the species. Width — Approximately 15 to 18 mm. Length — Approximately 20 to 22 mm.

*Petal form*.—Broadly ovate.

*Petal count*.—Nearly always 5.

*Petal color*.—Light pink when young (Red-Purple Group 62D, 65C-D, 69A-B and 73D), becoming darker near the petal claw.

*Flower arrangement of petals*.—Overlapping.

*Petal claw*.—Form — The claw is considered truncate in shape and has a medium size when compared to other varieties. Length — Approximately 1 to 2 mm. Width — Approximately 1 mm.

*Petal margins*.—Generally considered variable, from nearly smooth to slightly undulate.

*Petal apex*.—Generally — The petal apices appear slightly domed.

*Flower pedicel*.—Length — Considered short, and having an average length of approximately 1 to 2 mm. Thickness — Considered average, approximately 1 to 2 mm. Color — A light green (Yellow-Green Group 144C-D and N144A-D).

*Floral nectaries*.—Color — Bright orange (Orange Group 25A-B and N25A-B). Calyx — Surface Texture — Generally glabrous. Color — Maroon with green (Yellow-Green Group 144C-D, N144A-D, Greyed-Red Group 178A, 181A and Greyed-Purple 183A-C). Sepals — Surface Texture — The surface has a short, fine, wooly and a gray-colored texture. Size — Average, and ovate in form. Color — Maroon with green (Yellow-Green Group 144C-D, N144A-D, Greyed-Red Group 178A, 181A and Greyed-Purple 183A-C). Anthers — General — Average in size for the species. Color — Medium yellow (approximately Yellow-Orange Groups 15B-C and 16A-C).

*Pollen production*.—Pollen is abundant, and is a golden-yellow color. (approximately Yellow Group 13A-C and Yellow-Orange Group 14C-D).

*Filaments*.—Size — Variable in length, approximately 14 to 20 mm, with the filaments longer than the pistil. Color — White when young (White Group 155A-D) and darkening to light pink (Red-Purple 62D, 65A-D and 69A) with advanced maturity.

*Anther position relative to the pistil and petals*.—Anthers generally higher than the pistils and equal to or higher than the petals on a fully open flower.

*Pistil*.—General — Average in size, but slightly shorter, relative to the general anther height, overall. Length — Approximately 10 to 13 mm, including the ovary. Color — Considered a very light green when young (Yellow-Green Group 144B-D and N144C-D), maturing to very light yellow green (Green-Yellow Group 1B-D) and developing a purplish-red color (Red-Purple 63B and 64C) with advancing senescence. Surface Texture — The variety has a long, silver white pubescent pistil (approximately White Group 155A-D).

Fruit:

*Maturity when described*.—The present variety of fruit is described, as it would be found in its firm ripe condition at full commercial maturity. Under the ecological conditions prevailing in the medium chill of Texas this cultivar is picked from late May to early June depending on the year and the site of the orchard. The average time of harvest for Fairfield, Tex. was June 10th which was about a week after 'June Gold'.

*Size*.—General — Medium to medium large for the season and considered uniform.

*Average cheek diameter*.—Approximately 62 to 67 mm.

*Average suture diameter*.—Approximately 58 to 63 mm.

*Average axial diameter*.—Approximately 32 to 35 mm.

*Fruit form*.—Generally considered flat with unequal halves. Generally the fruit exhibits less symmetry when comparing the suture height with the line opposite the suture. The fruit is relatively uniform in symmetry when viewed from the apical aspect.

*Fruit suture*.—Generally, the suture protrudes slightly or is within 2-3 mm of being even and appears as a thin line with some stitching that extends from the base to the apex.

*Color*.—Generally, a combination of the ground and blush colors.

*Ventral surface*.—Form .— Considered relatively uniform.

*Stem cavity*.—Size — Considered moderately shallow for the species. Width — Approximately 6 to 8 mm. Length — Approximately 9 to 10 mm. Depth — Approximately 2 to 3 mm.

*Fruit base*.—Flat.

*Fruit apex*.—Flat.

*Fruit stem*.—Length — 9 to 10 mm. Thickness — Approximately 2 mm. Color — Medium to light green with yellowish green coloration (Yellow-Green Groups 144A-D and N144A).

*Fruit skin*.—Generally considered average in thickness. Surface Texture — Light, short pubescence. Skin Acidity — Subacid. Tenacious to Flesh — Yes at commercial maturity. Tendency to Crack — Not observed. Skin Color — Generally — Variable, with approximately 50-80% of the fruit surface covered with an attractive orange red blush. Down — Light and short. Blush Color — The blush ranges from an orange-yellow, medium orange, orange-red, dark red to very dark red (Yellow-Orange Groups 19A and 20A-B; Orange Group N25A; Orange-Red Groups 31A-B, 32B-C and N34A; and Red Groups 46A and 53A-B) with many degrees of shading and blending between these colorations. Skin Ground Color — Medium yellow (Yellow-Orange Groups 15B-D and 16B-D).

*Flesh color*.—Medium to light yellow (Yellow-Orange Groups 14B-C, 15C-D and 16B-C).

*Flesh fibers*.—Present, numerous and lightly colored. These fibers are present throughout the flesh.

*Stone cavity color*.—Generally considered medium yellow (Yellow-Orange Groups 14B-C, 15C-D and 16B-C) with a small amount of red (similar to Red Group 53B).

*Flesh texture*.—Generally, the flesh is considered firm and fine at commercial maturity.

*Ripening*.—Generally the fruit of the present variety ripens evenly.

*Flavor*.—Considered sweet with a sub-acid flavor.

*Soluble solids*.—Range from 11-18 Brix. The average Brix is 14.

*Titratable acidity*.—Generally between 0.2-0.4 Eq W/1000 mL of juice.

*Aroma*.—Pleasant and reasonably abundant.

*Eating*.—Generally considered very good.

Stone:

*Attachment*.—Semifreestone at commercial maturity.

*Stone size*.—Generally considered small relative to the ratio of stone to fruit size. Length — Approximately 12 to 15 mm. Width — Approximately 20 to 21 mm. Thickness — Approximately 17 to 19 mm.

*Fibers*.—Generally very few short fibers are attached along the surface of the stone.

*Stone form*.—Flat.

*Stone base*.—Wide.

*Apex shape*.—Very wide.

*Stone shape*.—The stone is normally flat.

*Stone surface*.—Surface Texture — Single pits with line grooves. Ridges — Numerous ridges are present basally, and converge towards the base of the stone. Ventral Edge — Medium. Dorsal Edge — Shape — Grooved and having moderately rough edges.

*Stone color*.—The color of the dry stone is a light to medium brown (Greyed-Yellow Group 161C-D, Greyed-Orange Groups 164D, 165D and 166D) with a slight red coloration (Similar to Red-Purple Group 58A). The color of the inside surface of the endocarp is primarily 165B-C and N167D of the Greyed-Orange Group.

*Tendency to split*.—Splitting is relatively uncommon.

*Kernel*.—The kernel fills the endocarp at harvest and measures approximately 5-7 mm in thickness, 6-9 mm in width, and 6-10 mm in length. The seed is not viable.

Use: The subject variety, 'Flat Delight Two', is a peach tree of early mid-season maturity, which produces fruit which are firm, attractively colored, and which are useful for both local fresh market and home garden use.

Keeping quality: Average.

Resistance to insects and disease: No particular susceptibilities were noted.

Shipping quality: Average.

Although the new variety of peach tree possesses the described characteristics when grown under the ecological conditions prevailing in the medium chill zone of Texas it will be understood that variations of the usual magnitude and characteristics incident to the changes in growing conditions, fertilization, pruning, and pest control are to be expected.

REFERENCES

Bailey, C. H., and L. F. Hough. 1983. Peach tree—N.J. F-2 cultivar. U.S. Plant Pat. No. 5,123. Oct. 18, 1983.

Brooks, R. M. 1958. Double Delight, Earligold, and June Gold peaches. Fruit Var. J. 3:22.

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Mehlenbacher, S. A., L. F. Hough, C. H. Bailey, and J. L. Frecon. 1985. 'Stark Saturn' peach. Fruit Var. J. 39(1):33. U.S. Plant Pat. No. 5,123. Oct. 18, 1983.

Ramming, D. W. 2005. 'Galaxy' peento peach. HortSci. 40 (6):

Sherman, W. B. and P. M. Lyrene. 1989. 'Flordacrest' peach. HortScience 24(2):394.

We claim:

1. A new and distinct *Prunus persica* tree, substantially as illustrated and described herein.

* * * * *